United States Patent
Kaneko

(10) Patent No.: US 10,571,404 B2
(45) Date of Patent: Feb. 25, 2020

(54) DEFECT INSPECTION APPARATUS, METHOD, AND PROGRAM

(71) Applicant: FUJIFILM Corporation, Tokyo (JP)

(72) Inventor: Yasuhiko Kaneko, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/015,614

(22) Filed: Jun. 22, 2018

(65) Prior Publication Data

US 2018/0299389 A1 Oct. 18, 2018

Related U.S. Application Data

(63) Continuation of application No. PCT/JP2016/080855, filed on Oct. 18, 2016.

(30) Foreign Application Priority Data

Jan. 29, 2016 (JP) .................. 2016-015666

(51) Int. Cl.
*G01N 21/88* (2006.01)
*G01B 11/06* (2006.01)
*G01B 11/22* (2006.01)

(52) U.S. Cl.
CPC ......... *G01N 21/8851* (2013.01); *G01B 11/06* (2013.01); *G01B 11/22* (2013.01); *G01N 2021/8887* (2013.01)

(58) Field of Classification Search
CPC .. G01N 23/18; G01N 21/8851; G01N 21/952; G01N 2021/888;
(Continued)

(56) References Cited

U.S. PATENT DOCUMENTS 5,095,204 A * 3/1992 Novini .............. G01N 21/9045
250/223 B
7,113,628 B1 9/2006 Obara et al.
(Continued)

FOREIGN PATENT DOCUMENTS

JP 9-113458 A 5/1997
JP 2001-156135 A 6/2001
(Continued)

OTHER PUBLICATIONS

International Search Report dated Dec. 20, 2016, issued by the International Searching Authority in application No. PCT/JP2016/080855.
(Continued)

*Primary Examiner* — Sang H Nguyen
(74) *Attorney, Agent, or Firm* — Sughrue Mion, PLLC

(57) ABSTRACT

To test object image data IMG1, images (possible-defect images D1 to D3) representing possible defects detected by an image processing unit 22 are added. Adjacent to sliders L1 and L2, a histogram H1 indicating the number of detected possible defects for each wall thickness and a histogram H2 indicating the number of detected possible defects for each size are displayed, respectively. When a checkbox CB1 corresponding to a type of defect is selected by an operation unit 14, only images of possible defects of the selected type are displayed on the test object image IMG1. When the sliders L1 and L2 are operated by the operation unit 14, only images of possible defects within a wall thickness range selected by the slider L1 and within a size range selected by the slider L2 are displayed, and images of possible defects outside the ranges are erased.

8 Claims, 9 Drawing Sheets

(58) Field of Classification Search
CPC ... G01N 2021/8887; G01N 2021/8854; G01B 15/02; G01B 11/06
See application file for complete search history.

(56) References Cited

U.S. PATENT DOCUMENTS

| | | | | |
|---|---|---|---|---|
| 8,879,055 | B1* | 11/2014 | Suzuki | G01N 21/956 356/237.1 |
| 9,244,024 | B1* | 1/2016 | Patterson | G01N 23/18 |
| 2001/0015415 | A1* | 8/2001 | Okamoto | G01N 21/9506 250/559.45 |
| 2002/0009220 | A1 | 1/2002 | Tanaka | |
| 2004/0018436 | A1* | 1/2004 | Ishikawa | G03F 1/84 430/5 |
| 2006/0274933 | A1 | 12/2006 | Obara et al. | |
| 2007/0055467 | A1* | 3/2007 | Tsuji | G01N 21/95607 702/81 |
| 2008/0187212 | A1 | 8/2008 | Obara et al. | |
| 2008/0226158 | A1 | 9/2008 | Abe et al. | |
| 2010/0310043 | A1 | 12/2010 | Shimada | |
| 2011/0168900 | A1* | 7/2011 | Dobbs | G01B 15/02 250/360.1 |
| 2011/0188734 | A1* | 8/2011 | Tsuchiya | G06T 7/0002 382/149 |
| 2011/0280470 | A1* | 11/2011 | Hayashi | G01N 21/9505 382/149 |
| 2014/0093139 | A1* | 4/2014 | Yamagishi | H04N 1/00034 382/112 |
| 2017/0241919 | A1* | 8/2017 | Machii | G01N 23/04 |

FOREIGN PATENT DOCUMENTS

| | | |
|---|---|---|
| JP | 2002-98653 A | 4/2002 |
| JP | 2002-181736 A | 6/2002 |
| JP | 2003-139723 A | 5/2003 |
| JP | 2006-12069 A | 1/2006 |
| JP | 2006-163608 A | 6/2006 |
| JP | 2007-24835 A | 2/2007 |
| JP | 2007-271316 A | 10/2007 |
| JP | 2007-305789 A | 11/2007 |
| JP | 2008-227028 A | 9/2008 |
| JP | 2010-281649 A | 12/2010 |
| JP | 2011-017694 A | 1/2011 |
| JP | 2012-145427 A | 8/2012 |
| JP | 2014-137281 A | 7/2014 |
| WO | 01/41068 A1 | 6/2001 |

OTHER PUBLICATIONS

International Preliminary on Patentability Report dated Sep. 4, 2017, issued by the International Searching Authority in application No. PCT/JP2016/080855.
Written Opinion dated Dec. 20, 2016, issued by the International Searching Authority in application No. PCT/JP2016/080855.
Communication dated Aug. 14, 2019, from the Japanese Patent Office in counterpart application No. 2017-563682.

* cited by examiner

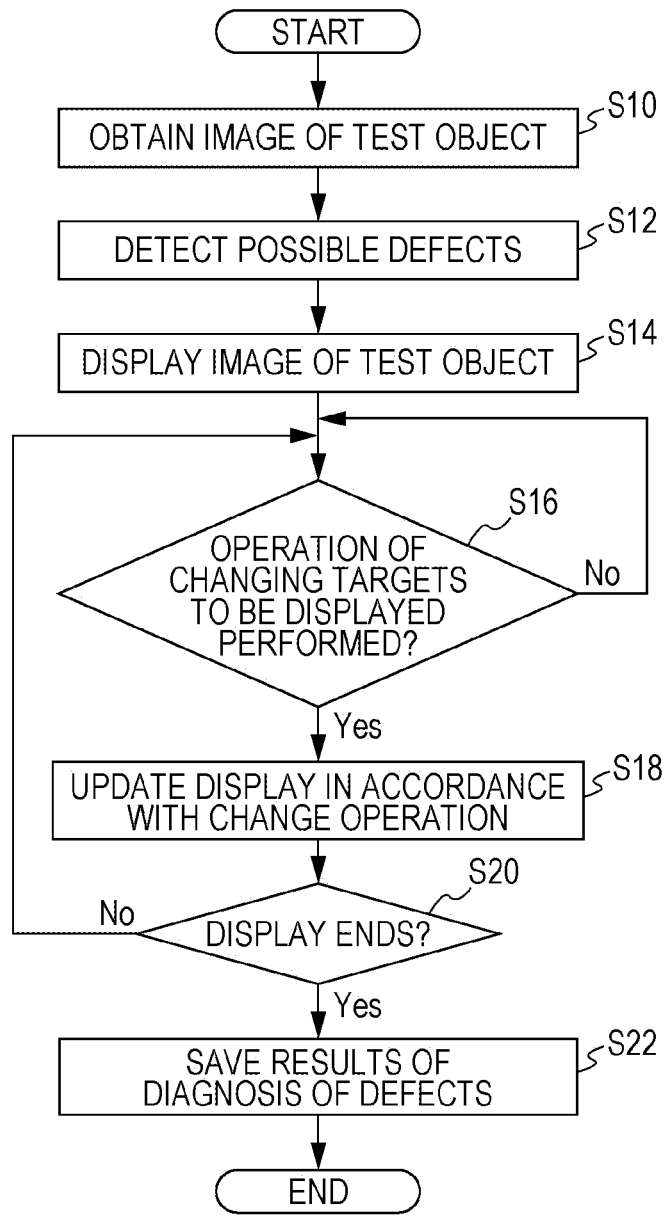

DEFECT INSPECTION APPARATUS, METHOD, AND PROGRAM

CROSS REFERENCE TO RELATED APPLICATIONS

This application is a Continuation of PCT International Application No. PCT/JP2016/080855 filed on Oct. 18, 2016, which claims priority under 35 U.S.C. § 119(a) to Patent Application No. 2016-015666 filed in Japan on Jan. 29, 2016, all of which are hereby expressly incorporated by reference into the present application.

BACKGROUND OF THE INVENTION

1. Field of the Invention

The present invention relates to a defect inspection apparatus, method, and program and specifically relates to a defect inspection apparatus, method, and program for providing assistance in inspecting defects using an image of an inspection-target industrial product.

2. Description of the Related Art

JP-2010-281649A discloses a radiographic inspection apparatus that irradiates an inspection target with radiation rays having different photon energies to obtain a plurality of radiographic images and generates a defect detection image on the basis of the plurality of radiographic images.

JP2014-137281A relates to a visual inspection of a nuclear power plant. JP2014-137281A discloses a GUI (graphical user interface) having an item in which a condition, a parameter group, or an individual parameter for image quality improvement processing can be selected by a user (inspector) and an item used by the user to variably adjust and set the value of the selected condition, parameter group, or parameter in a condition adjustment area (paragraphs <0135> to <0146>, FIG. 12, and FIG. 13).

SUMMARY OF THE INVENTION

In a case where an accident has once occurred in a facility, such as a pipeline, used to, for example, carry oils, the accident causes serious damage to society. It is difficult to remove a facility, such as a pipeline, for inspection, and therefore, a facility, such as a pipeline, is usually inspected by using a nondestructive inspection that involves irradiation of an inspection target, such as a pipeline, with light rays or radiation rays. In a nondestructive inspection, an image of an inspection target, such as a pipeline, obtained by irradiating the pipeline with light rays or radiation rays is interpreted by an image interpreter to check defects. In an inspection, various types of defects are detected, such as stains, cracks, dust, and chipping, which vary in form and size, and furthermore, a considerable number of defects are detected. Therefore, it takes a considerable time to exhaustively check these defects. Accordingly, it is required to increase precision and efficiency in interpretation of an image and checking of defects.

However, JP-2010-281649A does not disclose a technique for increasing precision and facilitating detection of defects from a defect detection image, and precision in defect detection may depend on the experience and capability of an image interpreter, which is a problem. JP2014-137281A discloses a GUI for a visual inspection of a nuclear power plant; however, the GUI is intended to improve image quality and is not intended to increase precision and facilitate defect detection.

The present invention has been made in view of the above-described circumstances, and an object thereof is to provide a defect inspection apparatus, method, and a non-transitory computer readable recording medium storing a program for, in a case of using an image of an inspection-target industrial product (hereinafter referred to as a test object) to conduct an inspection to check whether defects are present, allowing an image interpreter to precisely and efficiently detect defects.

To address the issues described above, a defect inspection apparatus according to a first aspect of the present invention includes: image obtaining means for obtaining a received-light image created on the basis of reflected light or transmitted light from a test object, the reflected light or the transmitted light being obtained as a result of irradiation of the test object with light rays or radiation rays; image processing means for calculating a position and features of each of possible defects in the test object from the received-light image; display means for displaying the received-light image, and displaying, on the received-light image, a calculation result regarding each of the possible defects obtained by the image processing means; and operation means for accepting an operation of changing a feature range of a possible defect to be displayed on the display means, and causing, in accordance with the operation, only a possible defect that falls within the feature range among the possible defects for which calculation is performed by the image processing means to be displayed on the received-light image displayed on the display means.

According to the first aspect, with the operation means, specification of the feature range of a possible defect to be displayed on the display means can be changed, and therefore, precision and efficiency in defect detection can be increased.

In a second aspect of the present invention, in the defect inspection apparatus according to the first aspect, the display means displays, on the received-light image, a mark for identifying the calculation result, which includes the position and the features of each of the possible defects, obtained by the image processing means.

According to the second aspect, the mark is displayed on the received-light image, and therefore, image interpretation of possible defects can be facilitated.

In a third aspect of the present invention, the defect inspection apparatus according to the first or second aspect further includes accepting means for accepting specification of an inspection area that is specified in advance on a per test-object basis. The display means displays, on the received-light image, a mark for specifically identifying the specified inspection area.

According to the third aspect, the inspection area specified by, for example, the manufacturer on the basis of the history of past defect occurrence, the occurrence frequency, and so on is presented to an image interpreter, and therefore, a defect diagnosis can be facilitated.

In a fourth aspect of the present invention, in the defect inspection apparatus according to any one of the first to third aspects, the operation means causes the display means to display, for each of the features of the possible defects, a slider bar for displaying a result of specification for the feature, and accepts an operation of moving a slider on the slider bar to thereby continuously or gradually change specification of the feature range.

According to the fourth aspect, with the use of the slider bar, specification of the feature range of a possible defect to be displayed on the display means can be continuously or gradually changed, and therefore, precision and efficiency in defect detection can be increased.

In a fifth aspect of the present invention, in the defect inspection apparatus according to the fourth aspect, the display means displays a frequency distribution indicating a detection frequency for each of the features of the possible defects in association with the slider bar.

According to the fifth aspect, with the frequency distribution (for example, a histogram), the image interpreter can recognize the detection frequency for each of the features of the possible defects and can operate the slider bar with reference to the detection frequency, and therefore, the image interpreter can efficiently operate the slider bar.

In a sixth aspect of the present invention, in the defect inspection apparatus according to any one of the first to fifth aspects, the operation means accepts an operation of continuously or gradually changing at least one of a wall thickness of the test object or a size of the possible defects as one of the features of the possible defects.

A defect inspection method according to a seventh aspect of the present invention includes: an image obtaining step of obtaining a received-light image created on the basis of reflected light or transmitted light from a test object, the reflected light or the transmitted light being obtained as a result of irradiation of the test object with light rays or radiation rays; an image processing step of calculating a position and features of each of possible defects in the test object from the received-light image; a display step of displaying, on display means of a defect inspection apparatus, the received-light image, and displaying, on the received-light image, a calculation result regarding each of the possible defects obtained in the image processing step; and a display control step of accepting, by operation means of the defect inspection apparatus, an operation of changing a feature range of a possible defect to be displayed on the display means, and causing, in accordance with the operation, only a possible defect that falls within the feature range among the possible defects for which calculation is performed in the image processing step to be displayed on the received-light image displayed on the display means.

A non-transitory computer readable recording medium storing a defect inspection program according to an eighth aspect of the present invention causes a computer to execute a function including: an image obtaining function of obtaining a received-light image created on the basis of reflected light or transmitted light from a test object, the reflected light or the transmitted light being obtained as a result of irradiation of the test object with light rays or radiation rays; an image processing function of calculating a position and features of each of possible defects in the test object from the received-light image; a display function of displaying, on display means of a defect inspection apparatus, the received-light image, and displaying, on the received-light image, a calculation result regarding each of the possible defects obtained by the image processing function; and a display control function of accepting, by operation means of the defect inspection apparatus, an operation of changing a feature range of a possible defect to be displayed on the display means, and causing, in accordance with the operation, only a possible defect that falls within the feature range among the possible defects for which calculation is performed by the image processing function to be displayed on the received-light image displayed on the display means.

According to the present invention, specification of the feature range of a possible defect to be displayed on the display means can be changed, and therefore, precision and efficiency in defect detection can be increased.

BRIEF DESCRIPTION OF THE DRAWINGS

FIG. 9 is a flowchart illustrating display control in a defect inspection method according to an embodiment of the present invention.

DESCRIPTION OF THE PREFERRED EMBODIMENTS

Hereinafter, a defect inspection apparatus, method, and program according to an embodiment of the present invention will be described with reference to the attached drawings.

Configuration of Defect Inspection Apparatus

Figure 1:
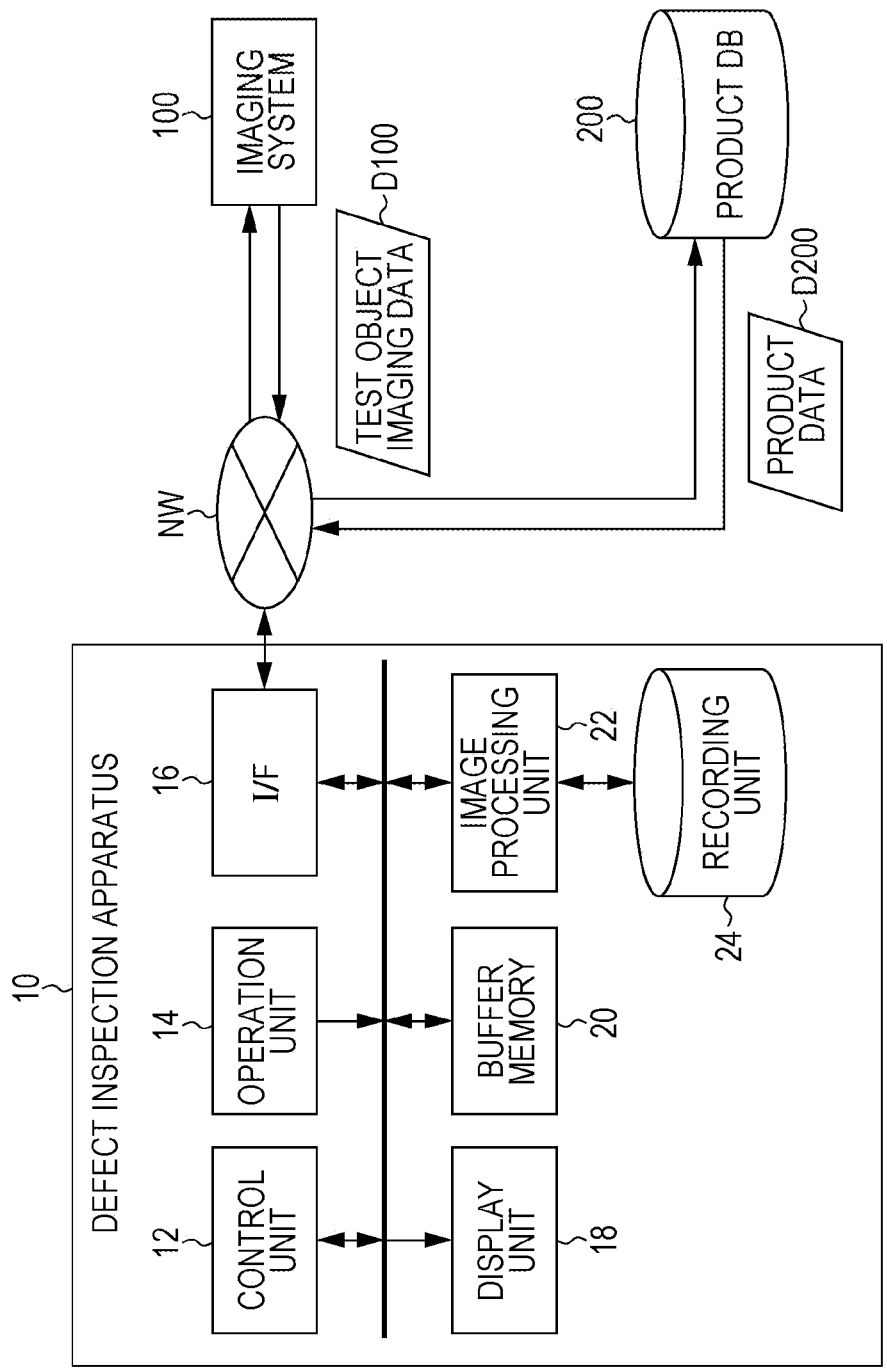
FIG. 1 is a block diagram illustrating a defect inspection apparatus according to an embodiment of the present invention.

FIG. 1 is a block diagram illustrating a defect inspection apparatus according to an embodiment of the present invention.

A defect inspection apparatus 10 according to this embodiment is an apparatus that detects possible defects from a captured image of an inspection-target industrial product (test object) and displays the possible defects, and is an apparatus for assisting an image interpreter in diagnosing a defect in the test object. As illustrated in FIG. 1, the defect inspection apparatus 10 according to this embodiment includes a control unit 12, an operation unit 14, an input/output interface (hereinafter referred to as an I/F (interface)) 16, a display unit 18, a buffer memory 20, an image processing unit 22, and a recording unit 24.

The control unit 12 includes a CPU (central processing unit) that controls the operations of the units of the defect inspection apparatus 10. The control unit 12 accepts an operation input by an image interpreter via the operation unit 14 and transmits a control signal corresponding to the input operation to the units of the defect inspection apparatus 10 to control the operations of the units.

The operation unit (operation means) 14 is an input device that accepts an operation input by an image interpreter, and includes a keyboard for inputting characters and a pointing device (for example, a mouse or a trackball) for operating, for example, pointers and icons displayed on the display unit 18. Note that, as the operation unit 14, a touch panel can be provided on the surface of the display unit 18 in place of the devices listed above or in addition to the devices listed above.

The I/F 16 is means for communication with an external apparatus via a network NW. As a method for data transmission/reception between the defect inspection apparatus 10 and an external apparatus, wired communication (for example, a LAN (local area network), a WAN (wide area network), or Internet connection) or wireless communication (for example, a LAN, a WAN, or Internet connection) can be used.

The defect inspection apparatus 10 can accept test object imaging data D100, which includes captured image data of a test object OBJ imaged by an imaging system 100 and is input via the I/F 16 (image obtaining means). Note that a method for inputting the test object imaging data D100 from the imaging system 100 to the defect inspection apparatus 10 is not limited to the communication listed above performed via the network NW. For example, the defect inspection apparatus 10 and the imaging system 100 may be connected to each other via, for example, a USB (Universal Serial Bus) cable, Bluetooth (registered trademark), or infrared communication. The test object imaging data D100 may be stored in a memory card that is mountable on and readable by the defect inspection apparatus 10, and the image data may be input to the defect inspection apparatus 10 via the memory card.

Furthermore, the defect inspection apparatus 10 can communicate with a product database (product DB) 200 via the network NW. In the product DB, product data D200 for each industrial product that can be an inspection target is stored. The control unit (accepting means) 12 can retrieve and read, from test object imaging data of the test object OBJ obtained from the imaging system 100, test object identification information for identifying the test object and obtain the product data D200 that corresponds to the read test object identification information from the product DB 200. When the product data D200 is used, possible defects in the test object OBJ can be detected in accordance with types or features.

Note that the product DB 200 may be placed on the network NW as in this embodiment to allow, for example, the manufacturer to update the product data D200, or may be provided in the defect inspection apparatus 10.

The display unit (display means) 18 is a device for displaying images. As the display unit 18, for example, a liquid crystal monitor (see FIG. 5) can be used.

The buffer memory 20 is used as a work area of the control unit 12 and an area for temporarily storing image data to be output to the display unit 18.

The recording unit 24 is means for storing data including a control program used by the control unit 12. As the recording unit 24, for example, a device, such as a magnetic disk, namely, an HDD (hard disk drive) or the like, or a device, such as a flash memory, namely, an eMMC (embedded Multi Media Card), an SSD (solid state drive), or the like, can be used. On the recording unit 24, the test object imaging data D100 and the product data D200 are stored.

The image processing unit (image processing means) 22 reads captured image data of the test object OBJ from the test object imaging data D100, performs image processing on the captured image data, and detects possible defects. The image processing unit 22 outputs the captured image data and pieces of possible-defect information indicating detection results (feature calculation results) of the detected possible defects to the buffer memory 20. The control unit 12 uses the data output to the buffer memory 20 to create a display image obtained by adding the pieces of possible-defect information to the captured image data and causes the display unit 18 to display the display image. Accordingly, an image interpreter can interpret the image displayed on the display unit 18 to inspect the test object OBJ.

The image interpreter can input, via the operation unit 14, a diagnosis result stating that, for example, "immediately replace the test object OBJ with a new one", "watch and wait (conduct a re-inspection a days after)", or "leave (not a defect)" for each piece of possible-defect information added to the image displayed on the display unit 18. The control unit 12 creates and stores on the recording unit 24 test object inspection result data D10 (see FIG. 3C), which includes the above-described diagnosis result data.

Figure 2:
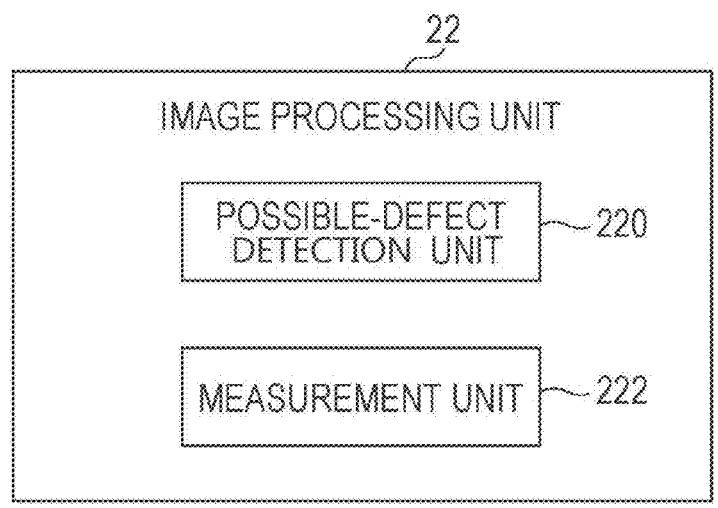
FIG. 2 is a block diagram illustrating an example of an image processing unit of the defect inspection apparatus according to an embodiment of the present invention.

FIG. 2 is a block diagram illustrating an example of the image processing unit. As illustrated in FIG. 2, the image processing unit 22 includes a possible-defect detection unit 220 and a measurement unit 222.

The possible-defect detection unit 220 performs image processing (for example, color conversion processing, monochrome conversion processing, edge enhancement processing, or 3D-data conversion processing) on captured image data to detect changes in, for example, the color of the test object OBJ, thereby detecting possible defects (for example, flaws, cracks, wear, and rust) in the test object OBJ. The possible-defect detection unit 220 detects defects on the basis of, for example, changes in color and edge detection results. Accordingly, the position and form of each possible defect are identified.

Note that, for example, product image data including an image of a (new) product that is identical to the test object OBJ and has no detected defects may be included in the product data D200, and the product image data may be compared with the captured image data of the test object OBJ to detect possible defects.

The measurement unit 222 measures the dimensions of each part of the test object OBJ on the basis of the captured image data of the test object OBJ and imaging condition data. The measurement unit 222 measures the size of the test object OBJ on the basis of the imaging condition data, which includes the distance between the camera and the test object OBJ, the focal length, and the zoom magnification at the time of imaging, and the magnitude of the test object OBJ in the captured image data. The measurement unit 222 uses the measured size of the test object OBJ and the magnitude of the test object OBJ and the magnitude of each possible defect in the captured image data to calculate the size of the possible defect (for example, the maximum dimensions, the minimum dimensions, or the depth and angle of a crack). Note that the size of the test object OBJ may be obtained from the product data D200.

Furthermore, the measurement unit 222 uses the dimensions of each part of the test object OBJ and information indicating, for example, the reflectance and light transmittance (transmission attenuation) of irradiation light at the time of imaging of the test object OBJ to measure the wall thickness of the test object OBJ at each position. Note that the wall thickness may be measured by the imaging system 100 at the time of imaging and included in the test object imaging data D100.

Figure 3A:
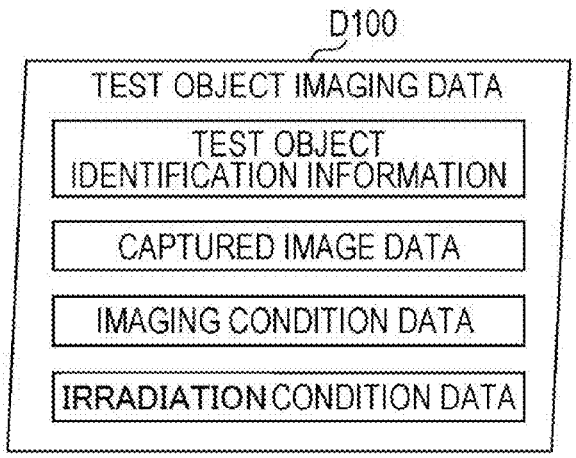
FIG. 3A is a block diagram illustrating an example of test object imaging data.

FIG. 3A is a block diagram illustrating an example of the test object imaging data. As illustrated in FIG. 3A, the test object imaging data D100 includes test object identification information, captured image data, imaging condition data, and irradiation condition data.

The test object identification information is information for identifying the test object OBJ and includes information indicating, for example, the product name, the product number, the manufacturer's name, and the technical classification of the test object OBJ.

The captured image data is image data (for example, an X-ray image or a visible-light image) obtained by imaging the test object OBJ.

The imaging condition data is stored for each piece of captured image data of the test object OBJ and includes information indicating the imaging date and time, the imaging target portion corresponding to the piece of captured image data, and the distance between the test object OBJ and the camera and the angle relative to the camera at the time of imaging.

The irradiation condition data includes information indicating the type of radiation (for example, X rays, visible rays, transmitted rays, or reflected rays) used to image the test object OBJ, the strength of irradiation, and the angle of irradiation.

Figure 3B:
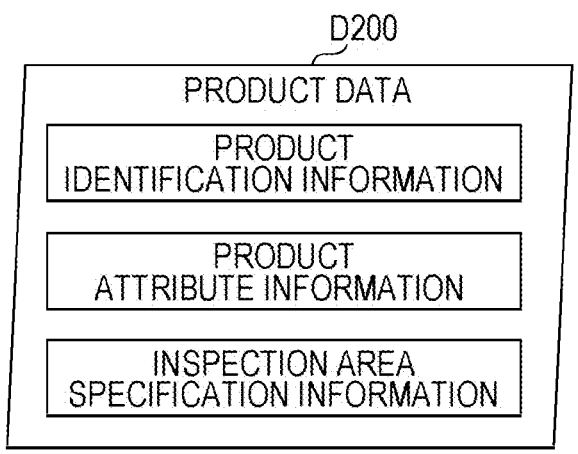
FIG. 3B is a block diagram illustrating an example of product data.

FIG. 3B is a block diagram illustrating an example of the product data. As illustrated in FIG. 3B, the product data includes product identification information, product attribute information, and inspection area specification information. The product data D200 may be associated with the test object imaging data D100 and the test object inspection result data D10 via the test object identification information and the product identification information and recorded to the recording unit 24, or may be obtained from the product DB 200 each time a defect inspection is conducted.

The product identification information is information for identifying the product and includes information indicating, for example, the product name, the product number, the manufacturer's name, and the technical classification.

The product attribute information includes information indicating, for example, the material and dimensions of each part of the product and the use of the product. The information indicating the use of the product includes information regarding, for example, the name and type of, for example, an apparatus in which the product is installed, and the state of processing and the method for installation (for example, a joint part, a welding part, fastening with screws, fitting, or soldering). The product attribute information further includes defect occurrence information. The defect occurrence information includes at least one piece of information among, for example, a past inspection date and time, the material of the test object OBJ, the type (for example, a foreign object or a crack), form, magnitude, depth, and site of occurrence (coordinates of site) of a defect occurred in the past, the wall thickness of the material, the state of processing (for example, a joint part or a welding part), frequency information regarding the defect occurrence frequency, and a captured image of the defect.

The inspection area specification information includes information indicating an inspection area specified by, for example, the manufacturer of the product (for example, information that includes the position of an inspection area and that is created on the basis of the defect occurrence information including information indicating whether a defect occurred in the past and the frequency information regarding the defect occurrence frequency). The inspection area specification information is created by identifying a portion in which a defect is likely to occur statistically or structurally on the basis of information regarding past repairs of the product by, for example, the manufacturer.

In a case of detecting possible defects from the test object OBJ, the image processing unit 22 can increase precision in detection of possible defects for an inspection area specified in the inspection area specification information (for example, decrease the minimum size (size threshold) of, for example, a flaw that is detected as a possible defect or decrease a threshold of the depth of a crack that is detected as a possible defect). When an image of the test object OBJ and images of possible defects are displayed on the display unit 18, the image processing unit 22 may add, for example, a mark for identifying captured image data of the inspection area and a mark for identifying a possible defect detected from a detection target area or may perform processing to emphasize the captured image data and the possible defect.

Note that, for a product having a plurality of uses, inspection area specification information may be created for each of the uses of the product (for example, for each of the types of apparatuses in which the product is installed or for each of the installation places), and possible defects may be detected by using inspection area specification information that corresponds to a specified use.

In a case where product data including a product name or a product number that matches the product name or the product number of the test object OBJ is not present, product data of a product having a technical classification similar to that of the test object OBJ may be obtained and used in image processing.

Figure 3C:
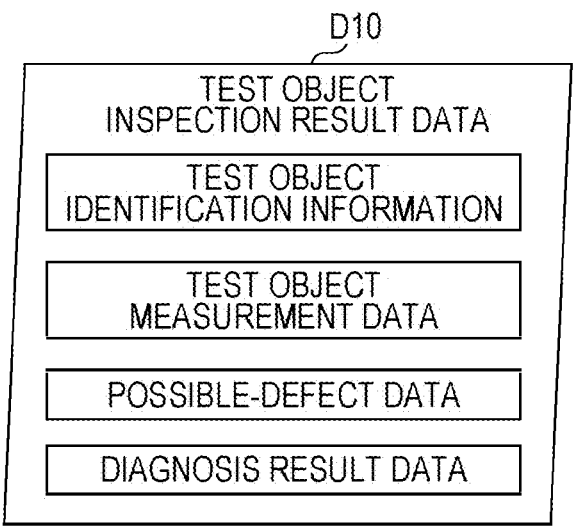
FIG. 3C is a block diagram illustrating an example of test object inspection result data.

FIG. 3C is a block diagram illustrating an example of the test object inspection result data. As illustrated in FIG. 3C, the test object inspection result data D10 includes test object measurement data, possible-defect dasta, and diagnosis result data in addition to the test object identification information described above. The test object inspection result data D10 is associated with the test object imaging data D100 via the test object identification information and recorded to the recording unit 24.

The test object measurement data includes information indicating the size of the test object OBJ and the wall thickness of the test object OBJ at each position obtained as a result of measurement by the measurement unit 222.

The possible-defect data includes information indicating the features of each possible defect (for example, the position, the size, the amount of change in wall thickness, and the type of each possible defect). The information indicating the position of each possible defect can be represented by, for example, coordinates in a coordinate system (for example, a 3D rectangular coordinate system, a polar coordinate system, or a cylindrical coordinate system) set in accordance with the form of the test object OBJ. The information indicating the type of each possible defect is information created on the basis of the form of the possible defect detected from an image and is information indicating, for example, a granular defect, a stain-like defect, or a crack-like defect.

The diagnosis result data includes the inspection date and time and information regarding each possible defect additionally input by an image interpreter. The diagnosis result data includes information indicating the result of diagnosis input by the image interpreter stating that, for example, "immediately replace the test object OBJ with a new one", "watch and wait (conduct a re-inspection n days after)", or "leave (not a defect)".

Note that the test object inspection result data D10 may include part of the test object imaging data D100 and the product data D200.

Furthermore, the test object inspection result data D10 may be transmitted and accumulated in the product DB 200, the possible-defect data and the diagnosis result data included in the test object inspection result data D10 may be analyzed, and the inspection area specification information in the product data D200 may be updated by using the result of analysis.

Configuration of Imaging System

Figure 4:
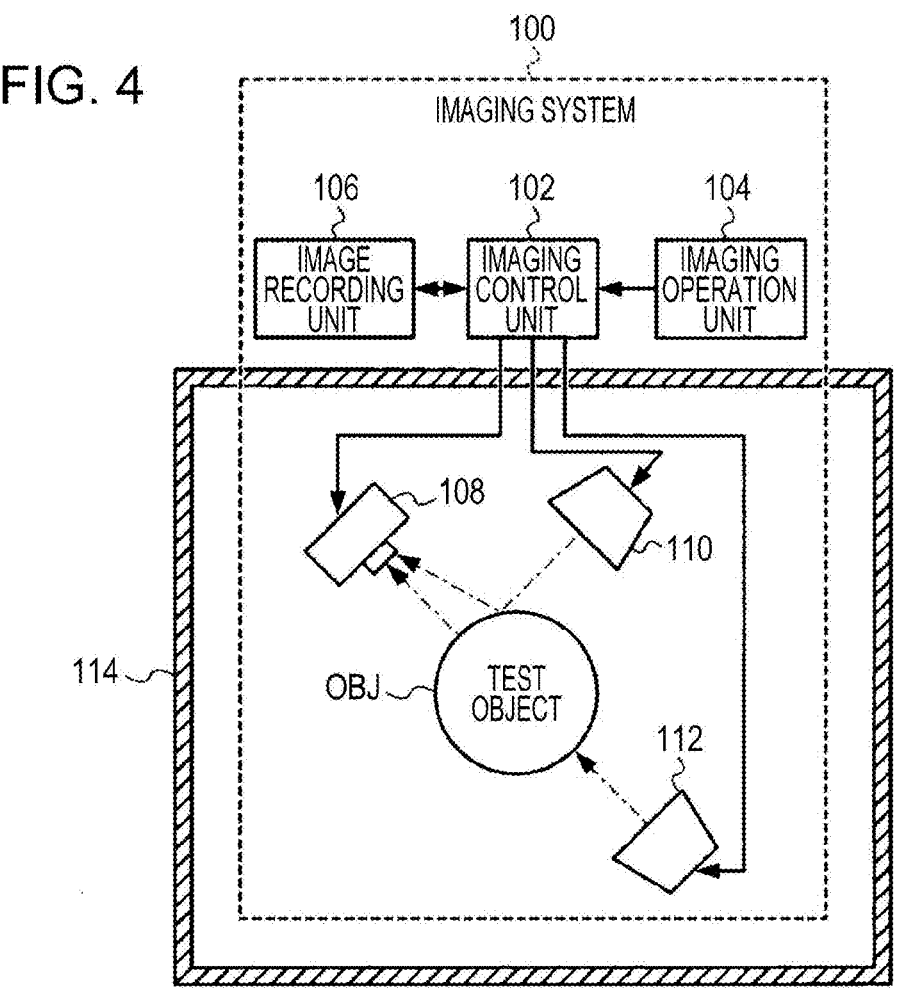
FIG. 4 is a block diagram illustrating an example of an imaging system.

Now, the imaging system 100 for capturing an image of the test object OBJ is described. FIG. 4 is a block diagram illustrating an example of the imaging system.

The imaging system 100 is a system for imaging the test object OBJ placed in an imaging room 114 and includes an imaging control unit 102, an imaging operation unit 104, an image recording unit 106, a camera 108, and radiation sources 110 and 112, as illustrated in FIG. 4.

The imaging control unit 102 includes a CPU (central processing unit) that controls the operations of the units of the imaging system 100. The imaging control unit 102 accepts an operation input by an operator (a person who performs imaging) via the imaging operation unit 104 and transmits a control signal corresponding to the input operation to the units of the imaging system 100 to control the operations of the units.

The imaging operation unit 104 is an input device that accepts an operation input by an operator, and includes a keyboard for inputting characters and a pointing device (for example, a mouse or a trackball) for operating, for example, pointers and icons displayed on the display unit 18. The operator can input object information regarding the test object OBJ, input an instruction (including imaging conditions, such as the exposure time, the focal length, and the aperture setting, and settings, such as the angle of imaging and the imaging portion) to be given to the camera 108 for performing imaging, input an instruction (including settings, such as the irradiation start time, the irradiation duration, the angle of irradiation, and the strength of irradiation) to be given to the radiation sources 110 and 112 for irradiation with radiation rays, and input an instruction for recording obtained image data to the image recording unit 106, via the imaging operation unit 104.

The image recording unit 106 records image data (received-light image) of the test object OBJ imaged by the camera 108. To the image recording unit 106, information for identifying the test object OBJ is recorded in association with the image data.

The camera 108 and the radiation sources 110 and 112 are arranged inside the imaging room 114. The radiation sources 110 and 112 are, for example, X-ray sources. The walls between the imaging room 114 and the outside and the door are provided with X-ray protection using an X-ray protective material (for example, lead or concrete). Note that, in a case of imaging by irradiating the test object OBJ with visible light, the imaging room 114 provided with protection need not be used.

The radiation sources 110 and 112 irradiate the test object OBJ placed inside the imaging room 114 with radiation rays in accordance with an instruction from the imaging control unit 102.

The camera 108 receives radiation rays emitted from the radiation source 110 to the test object OBJ and reflected by the test object OBJ or radiation rays emitted from the radiation source 112 to the test object OBJ and passing through the test object OBJ in accordance with an instruction from the imaging control unit 102 for performing imaging to thereby image the test object OBJ. The test object OBJ is held by a holding member not illustrated (for example, a manipulator, a mounting table, or a movable mounting table) inside the imaging room 114, and the distances from the test object OBJ to the camera 108 and to the radiation sources 110 and 112 and the angles of the test object OBJ relative to the camera 108 and to the radiation sources 110 and 112 can be adjusted. An operator can control the relative positions of the test object OBJ, the camera 108, and the radiation sources 110 and 112 and can image a desired portion of the test object OBJ, via the imaging control unit 102.

The radiation sources 110 and 112 stop irradiating the test object OBJ with radiation rays in synchronization with the end of imaging performed by the camera 108.

Note that, in the example illustrated in FIG. 4, the camera 108 is arranged inside the imaging room 114; however, the camera 108 may be arranged outside as long as the test object OBJ inside the imaging room 114 can be imaged.

In the example illustrated in FIG. 4, one camera, namely, the camera 108, and two radiation sources, namely, the radiation sources 110 and 112, are provided; however, the number of cameras and the number of radiation sources are not limited to these. For example, a plurality of cameras and a plurality of radiation sources may be provided, or one camera and one radiation source may be provided.

Display Control for Image of Test Object

Now, examples of display control for an image of a test object according to this embodiment are described.

Figure 5:
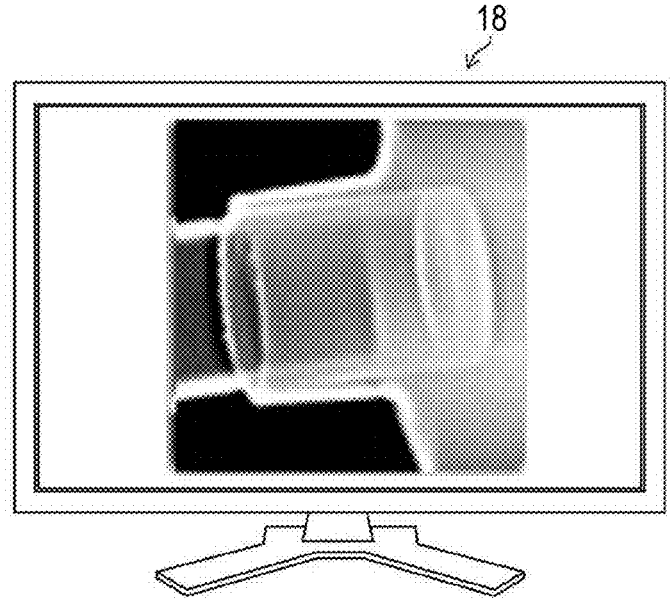
FIG. 5 is a front view illustrating the external appearance of a display unit of the defect inspection apparatus according to an embodiment of the present invention.
Figure 6:
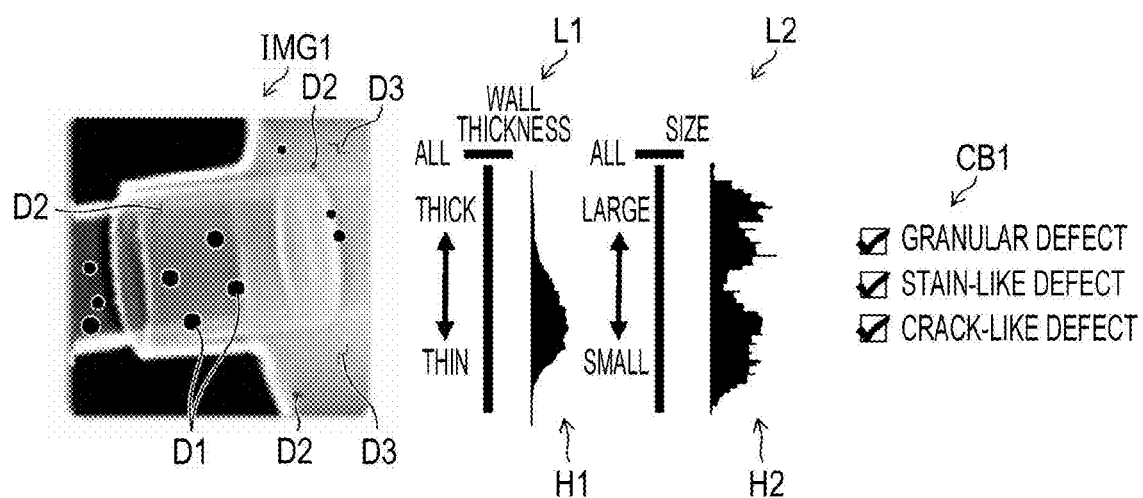
FIG. 6 is a diagram illustrating example display of possible defects.

FIG. 5 is a front view illustrating the external appearance of the display unit of the defect inspection apparatus according to an embodiment of the present invention. FIG. 6 is a diagram illustrating example display of possible defects.

As illustrated in FIG. 6, on the display unit 18, the test object image IMG1 of the test object OBJ and GUIs (graphical user interfaces) for changing display targets are displayed.

To the test object image data IMG1, images that represent possible defects detected by the image processing unit 22 (hereinafter referred to as possible-defect images D1 to D3) are added. The possible-defect images D1 to D3 can be, for example, color-coded and displayed in accordance with the types. In the example illustrated in FIG. 6, as the types of possible defects, three types including "granular defect", "stain-like defect", and "crack-like defect" are presented, which are illustrated as possible defects D1, D2, and D3 respectively. Note that the types of possible defects are not limited to these and, for example, an image interpreter may be allowed to change the settings using the operation unit 14.

The checkboxes CB1 are GUIs for selecting types of defects to be displayed on the test object image IMG1. When the checkboxes CB1 for "granular defect", "stain-like defect", and/or "crack-like defect" are selected by the operation unit 14, the control unit 12 displays only images of possible defects of the one or more selected types on the test object image IMG1. For example, when "granular defect" is selected, only the possible-defect images D1 are displayed on the test object image IMG1, and the possible-defect images D2 and D3 that are displayed are erased. An image interpreter can select one or more types of defects to be displayed from among "granular defect", "stain-like defect", and "crack-like defect" by operating the checkboxes CB1 via the pointing device of the operation unit 14.

The sliders (slider bars) L1 and L2 are GUIs for continuously or gradually changing the wall thickness around a defect and size of a defect to be displayed on the test object image IMG1, respectively. Adjacent to the sliders L1 and L2, the histograms H1 and H2 are respectively displayed. The histogram H1 indicates the frequency distribution of the detection frequency of possible defects for each wall thickness, and the histogram H2 indicates the frequency distribution of the detection frequency of possible defects for each size.

In the example illustrated in FIG. 6, setting is performed to display "all" for both the wall thickness and the size, and possible defects in all portions of the test object OBJ are displayed. When the sliders L1 and L2 are operated (moved) by the operation unit 14, only images of possible defects within a wall thickness range selected by the slider L1 and within a size range selected by the slider L2 are displayed, and images of possible defects outside the ranges are erased.

Note that, in this embodiment, the wall thickness of a portion in which a possible defect is detected and the size of a possible defect are continuously or gradually changed by using the GUIs, namely, the sliders L1 and L2, respectively, to thereby enable selection of possible defects to be displayed; however, this embodiment is not limited to this configuration. For example, a numerical value or a numerical range (hereinafter referred to as a numerical value or the like) indicating a wall thickness or a size input via the operation unit 14 may be accepted, and only possible defects corresponding to the input numerical value or the like may be selectively displayed. In a case of accepting input of a numerical range, an upper limit or a lower limit input via the operation unit 14 may be accepted, and only possible defects corresponding to a wall thickness equal to or lower than the input upper limit or equal to or higher than the input lower limit or only possible defects having a size equal to or lower than the input upper limit or equal to or higher than the input lower limit need to be displayed.

Furthermore, numerical values or numerical ranges specified by the sliders L1 and L2 may be displayed together with the sliders L1 and L2 of this embodiment. In a case of displaying the sliders L1 and L2 and the numerical values or the like together, the numerical values or the like to be displayed may be updated by the control unit 12 in accordance with operations of the sliders L1 and L2, or the sliders L1 and L2 may be moved in accordance with numerical values input from the operation unit 14. The widths of the sliders L1 and L2 of the respective slider bars, which represent the ranges of numerical values that can be specified by the sliders L1 and L2, may be changeable in accordance with drag operations by the operation unit 14 or numerical values input from the operation unit 14. For example, in a case where 1 µm is specified as the width represented by the slider L1, the position of the slider L1 is assumed to be the reference, and only possible defects within a range of ±0.5 µm need to be displayed on the display unit 18. Note that, in a case of changing the widths of the sliders L1 and L2 by drag operations, numerical values representing the widths of the sliders L1 and L2 may be updated and displayed in conjunction with the drag operations.

FIGS. 7A to 7D illustrate changes in display when the sliders are moved. In the example illustrated in FIG. 7A, the slider L1 is moved to a position at which the number of detected possible defects reaches its peak in the histogram H1, and the slider L2 is moved to a position at which the number of detected possible defects reaches its peak in the histogram H2. When the slider L1 is moved to the position at which the number of detected possible defects reaches its peak, a portion in which a large number of possible defects are detected, that is, a portion in which defects seem to frequently occur, can be identified. When the slider L2 is moved to the position at which the number of detected possible defects reaches its peak, an image interpreter can estimate the size of defects that frequently occur.

Figure 7A:
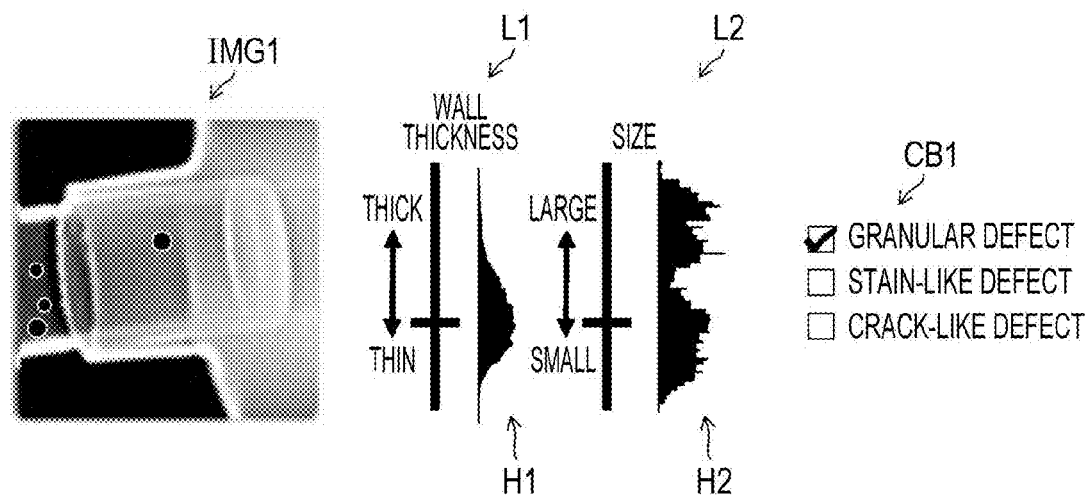
FIG. 7A is a diagram illustrating example display control (display target change) according to an embodiment of the present invention.
Figure 7B:
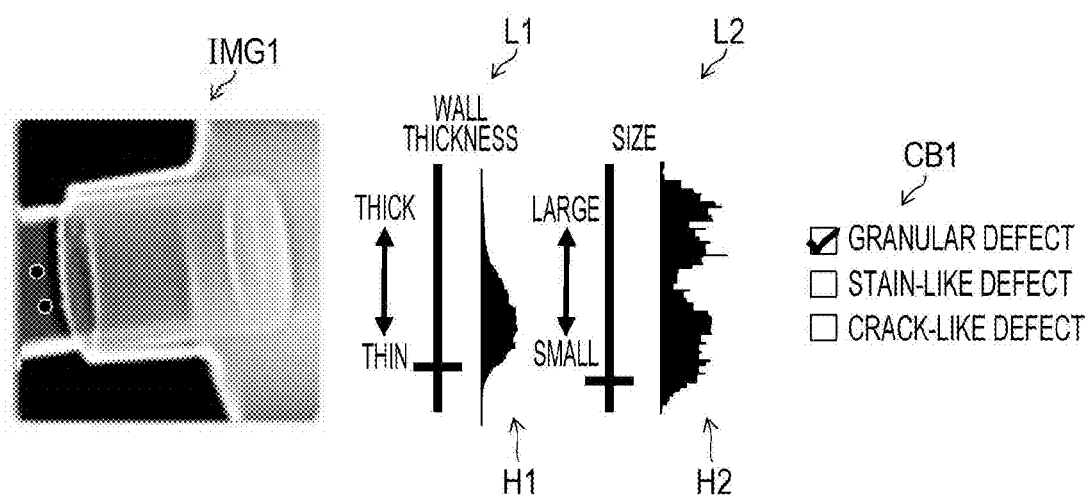
FIG. 7B is a diagram illustrating example display control (display target change) according to an embodiment of the present invention.

In the example illustrated in FIG. 7B, the sliders L1 and L2 are set so as to display images of possible defects having a relatively small size and detected in portions having a relatively small wall thickness in the test object OBJ.

Figure 7C:
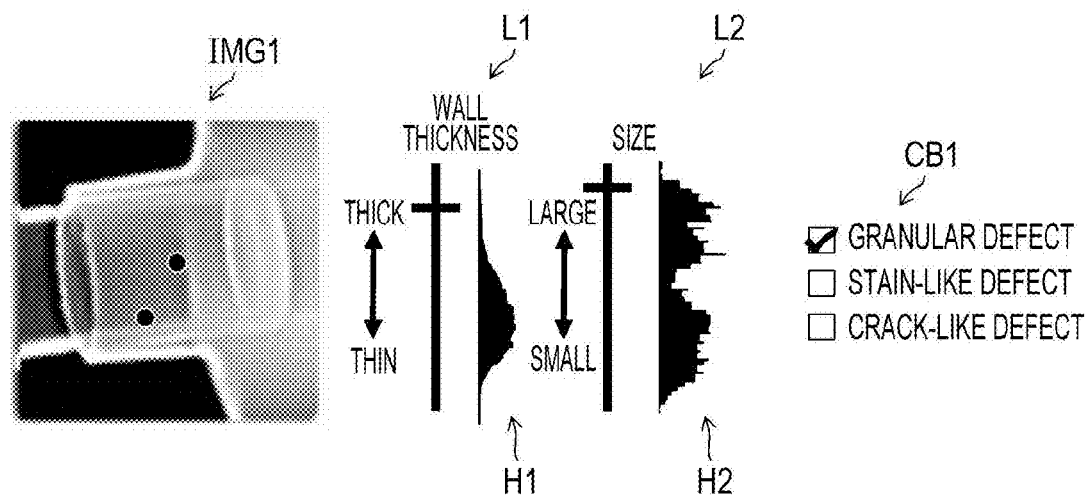
FIG. 7C is a diagram illustrating example display control (display target change) according to an embodiment of the present invention.

In the example illustrated in FIG. 7C, the sliders L1 and L2 are set so as to display images of possible defects having a relatively large size and detected in portions having a relatively large wall thickness in the test object OBJ.

Figure 7D:
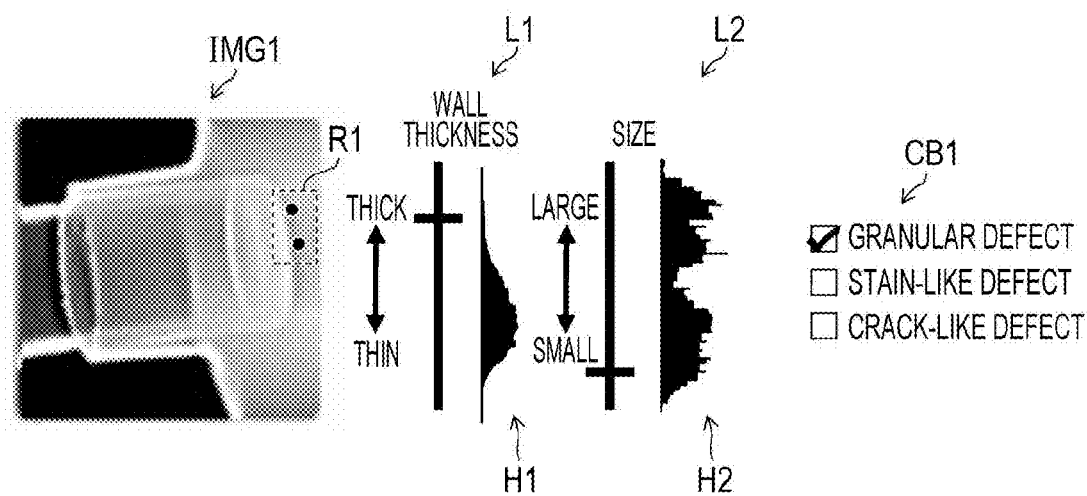
FIG. 7D is a diagram illustrating example display control (display target change) according to an embodiment of the present invention.

In the example illustrated in FIG. 7D, the sliders L1 and L2 are set so as to display images of possible defects having a relatively small size and detected in portions having a relatively large wall thickness in the test object OBJ. In the example illustrated in FIG. 7D, the outline R1, which indicates an inspection area specified in the inspection area specification information, is displayed. Accordingly, an image interpreter can recognize the inspection area specified in advance as a portion in which the possibility of defect occurrence is relatively high.

Figure 8A:
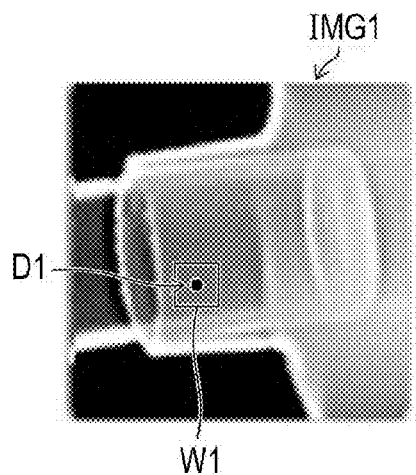
FIG. 8A is a diagram illustrating example display control (display area change) according to an embodiment of the present invention.
Figure 8B:
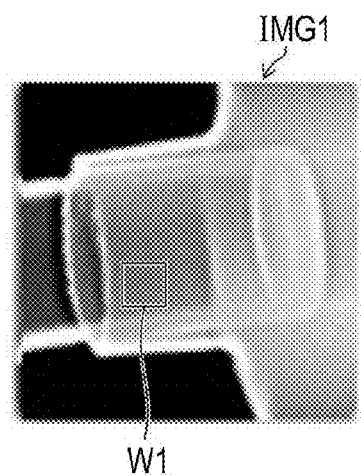
FIG. 8B is a diagram illustrating example display control (display area change) according to an embodiment of the present invention.
Figure 8C:
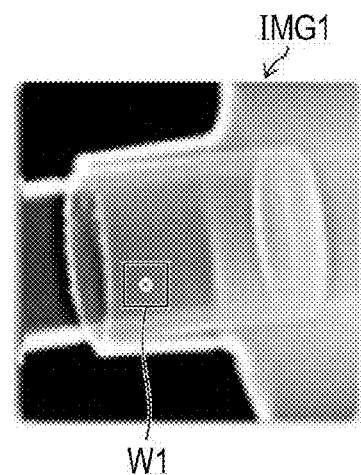
FIG. 8C is a diagram illustrating example display control (display area change) according to an embodiment of the present invention.

FIGS. 8A to 8C are diagrams illustrating example display control (display area change) according to an embodiment of the present invention.

In the example illustrated in FIG. 8A, the partial enlargement window W1 is displayed on the test object image IMG1, and the possible-defect image D1 is displayed only within the partial enlargement window W1. The partial enlargement window W1 can be moved by the operation unit 14.

In the example illustrated in FIG. 8B, a possible-defect image displayed within the partial enlargement window W1 is erased by the operation unit 14. Accordingly, an image interpreter can observe in detail the image of the area enlarged by the partial enlargement window W1.

In the example illustrated in FIG. 8C, a possible-defect image displayed within the partial enlargement window W1 is erased, and the shades of the image within the partial enlargement window W1 are converted to a hue map. Accordingly, changes in color that are difficult to observe in the image before conversion can be read.

Defect Inspection Method

FIG. 9 is a flowchart illustrating display control in a defect inspection method according to an embodiment of the present invention.

First, the defect inspection apparatus 10 obtains the test object imaging data D100 including an image (captured image data) of a test object from the imaging system 100 via the I/F 16 (step S10: image obtaining step). The image processing unit 22 performs image processing on the captured image data obtained in step S10 to detect possible defects (step S12: image processing step). The control unit 12 creates a display image on the basis of the captured image data obtained in step S10 and the results of detection of possible defects in step S12 and outputs the display image to the display unit 18. Accordingly, the test object image IMG1 to which possible-defect images are added is displayed on the display unit 18 (step S14: display step).

Next, if the control unit 12 accepts a change operation of changing targets to be displayed via GUIs, such as the checkboxes CB1 and the sliders L1 and L2 (Yes in step S16), the control unit 12 updates display on the display unit 18 in accordance with the change operation (step S18: display control step). For example, in a case where the slider L1 for the wall thickness is operated, only possible defects in parts having a wall thickness that is within a range specified by the slider L1 are displayed.

If the inspection by the image interpreter ends and an instruction for ending display is input by the operation unit 14 (Yes in step S20), the results of diagnosis of defects are included in the test object inspection result data D10 as the diagnosis result data, and the data is recorded to the recording unit 24 (step S22).

According to this embodiment, possible defects can be detected by the image processing unit 22, specification of the ranges of the features of possible defects to be displayed on the display unit 18 can be changed continuously or gradually, and GUIs for operations of interactively changing possible defects to be displayed can be provided. Accordingly, the effects of the experience and capability of an image interpreter on precision and efficiency in defect detection can be reduced, and a very small defect or a very small change in hue that an image interpreter usually has difficulty in detecting can be precisely and efficiently detected, and therefore, precision and efficiency in defect detection can be increased.

The present invention can be implemented as a program (defect inspection program) for causing a computer to implement the above-described processing or as a non-transitory recording medium or a program product in which such a program is stored. When such a defect inspection program is applied to a computer, arithmetic means, recording means, and so on of the computer can be caused to function as an image obtaining function, an image processing function, a display function, and a display control function of the defect inspection program.

REFERENCE SIGNS LIST 10 defect inspection apparatus
12 control unit
14 operation unit
16 input/output interface (I/F)
18 display unit
20 buffer memory
22 image processing unit
24 recording unit
220 possible-defect detection unit
222 measurement unit
S10 to S22 each step in display control

What is claimed is:

1. A defect inspection apparatus comprising:
an instruction input user interface that inputs at least one of an irradiation start time, an irradiation duration, an angle of irradiation, and a strength of irradiation for radiation rays which irradiates an test object;
an image obtaining interface that obtains a received-light image created on the basis of transmitted light from the test object, the transmitted light being obtained as a result of irradiation of the test object with radiation rays in accordance with the instruction by the instruction input user interface;
an image processing unit that calculates a position and features of each of possible defects in the test object from the received-light image;
a display unit that displays the received-light image, and displays, on the received-light image, a calculation result regarding each of the possible defects obtained by the image processing unit;
an operation unit that accepts an operation of changing a range of the features of the possible defects to be displayed on the display unit, and causes, in accordance with the operation, only the possible defects that fall within the range of the features among the possible defects for which calculation is performed by the image processing unit to be displayed on the received-light image displayed on the display unit; and
an accepting unit that accepts specification of an inspection area that is specified in advance on a per test-object basis, based on a defect occurrence information,
wherein the display unit displays, on the received-light image, a mark for identifying the content of the specification of the specified inspection area; and
wherein the operation unit causes the display unit to display, for each of the features of the possible defects, a slider bar for displaying a result of specification for the feature, and accepts an operation of moving a slider on the slider bar to thereby continuously or gradually change specification of the range of the features.

2. The defect inspection apparatus according to claim 1, wherein
the display unit displays, on the received-light image, a mark for identifying the calculation result, which includes the position and the features of each of the possible defects, obtained by the image processing unit.

3. The defect inspection apparatus according to claim 2, wherein
the operation unit accepts an operation of continuously or gradually changing at least one of a wall thickness of the test object or a size of the possible defects as one of the features of the possible defects.

4. The defect inspection apparatus according to claim 1, wherein
the display unit displays a frequency distribution indicating a detection frequency for each of the features of the possible defects in association with the slider bar.

5. The defect inspection apparatus according to claim 4, wherein
the operation unit accepts an operation of continuously or gradually changing at least one of a wall thickness of the test object or a size of the possible defects as one of the features of the possible defects.

6. The defect inspection apparatus according to claim 1, wherein
the operation unit accepts an operation of continuously or gradually changing at least one of a wall thickness of the test object or a size of the possible defects as one of the features of the possible defects.

7. A defect inspection method comprising:
an instruction input step that inputs at least one of an irradiation start time, an irradiation duration, an angle of irradiation, and a strength of irradiation for radiation rays which irradiates an test object;
an image obtaining step that obtains a received-light image created on the basis of transmitted light from the test object, the transmitted light being obtained as a result of irradiation of the test object with radiation rays;
an image processing step that calculates a position and features of each of possible defects in the test object from the received-light image;
a display step that displays, on a display unit of a defect inspection apparatus, the received-light image, and displays, on the received-light image, a calculation result regarding each of the possible defects obtained in the image processing step;
a display control step that accepts, by operation unit of the defect inspection apparatus, an operation of changing a range of the features of the possible defects to be displayed on the display unit, and causes, in accordance with the operation, only the possible defects that fall within the range of features among the possible defects for which calculation is performed in the image processing step to be displayed on the received-light image displayed on the display unit; and
an accepting step that accepts specification of an inspection area that is specified in advance on a per test-object basis, based on a defect occurrence information,
wherein the display unit displays, on the received-light image, a mark for identifying the content of the specification of the specified inspection area; and
wherein the operation unit causes the display unit to display, for each of the features of the possible defects, a slider bar for displaying a result of specification for the feature, and accepts an operation of moving a slider on the slider bar to thereby continuously or gradually change specification of the range of the features.

8. A non-transitory computer readable recording medium storing a defect inspection program causing a computer to execute a function comprising:
an instruction input function that inputs at least one of an irradiation start time, an irradiation duration, an angle of irradiation, and a strength of irradiation for radiation rays which irradiates an test object;
an image obtaining function that obtains a received-light image created on the basis of reflected light or transmitted light from the test object, the transmitted light being obtained as a result of irradiation of the test object with radiation rays;
an image processing function that calculates a position and features of each of possible defects in the test object from the received-light image;
a display function that displays, on a display unit of a defect inspection apparatus, the received-light image, and displays, on the received-light image, a calculation result regarding each of the possible defects obtained by the image processing function;
a display control function that accepts, by operation unit of the defect inspection apparatus, an operation of changing a range of the features of the possible defects to be displayed on the display unit, and causes, in accordance with the operation, only the possible defects that falls within the range of features among the possible defects for which calculation is performed by the image processing function to be displayed on the received-light image displayed on the display unit; and
an accepting step that accepts specification of an inspection area that is specified in advance on a per test-object basis, based on a defect occurrence information,
wherein the display unit displays, on the received-light image, a mark for identifying the content of the specification of the specified inspection area; and
wherein the operation unit causes the display unit to display, for each of the features of the possible defects, a slider bar for displaying a result of specification for the feature, and accepts an operation of moving a slider on the slider bar to thereby continuously or gradually change specification of the range of the features.

\* \* \* \* \*